United States Patent [19]

Tycko

[11] Patent Number: 5,194,909
[45] Date of Patent: Mar. 16, 1993

[54] APPARATUS AND METHOD FOR MEASURING VOLUME AND HEMOGLOBIN CONCENTRATION OF RED BLOOD CELLS

[76] Inventor: Daniel H. Tycko, P.O. Box 1033, Stony Brook, N.Y. 11790

[21] Appl. No.: 621,899

[22] Filed: Dec. 4, 1990

[51] Int. Cl.$^5$ .......................................... G01N 33/48
[52] U.S. Cl. ..................... 356/40; 356/335; 356/336; 356/337; 356/340; 356/73; 422/82.05; 436/164; 435/808
[58] Field of Search ................ 356/40, 72, 335, 336, 356/337, 338, 339, 340, 341, 342, 343, 73; 422/82.05, 82.11; 436/164; 435/808

[56] References Cited

U.S. PATENT DOCUMENTS

| | | | |
|---|---|---|---|
| 2,656,508 | 10/1953 | Coulter | 324/71.1 |
| 3,661,460 | 5/1972 | Elking | 356/36 |
| 3,710,933 | 1/1973 | Fulwyler et al. | 209/3.1 |
| 3,890,568 | 6/1975 | Coulter et al. | 377/11 |
| 4,198,160 | 4/1980 | Kachel et al. | 356/72 |
| 4,298,836 | 11/1981 | Groves et al. | 324/71.1 |
| 4,303,337 | 12/1981 | James et al. | 356/40 |
| 4,348,107 | 9/1982 | Leif | 356/72 |
| 4,412,004 | 10/1983 | Ornstein et al. | 436/10 |
| 4,510,438 | 4/1985 | Auer | 356/335 |
| 4,735,504 | 4/1988 | Tycko | 356/336 |

OTHER PUBLICATIONS

J. T. Merrill et al., "An Improved Cell Volume Analyzer", The Review of Scientific Instruments, Aug. 1971, vol. 42, No. 8, pp. 1157–1163.
R. C. Leif et al., "Electronic Cell-Volume Analysis by Use of the AMAC I Transducer", Clin. Chem., 1973, vol. 19, No. 8, pp. 853–870.
J. A. Steinkamp et al., "A New Multiparameter Separator for Microscopic Particles and Biological Cells", Rev. Sci. Instrum., Sep. 1973, vol. 44, No. 9, pp. 1301–1310.
R. A. Thomas, et al., "Computer-Based Electronic Cell Volume Analysis with the AMAC II Tranducer", The Journal of Histochemistry and Cytochemistry, 1974, vol. 22, No. 7, pp. 626–641.
V. Kachel, "Basic Principles of Electrical Sizing of Cells and Particles and Their Realization in the New Instrument 'Metricell'", The Journal of Histochemistry and Cytochemistry, 1976, vol. 24, No. 1, pp. 211–230.
R. A. Thomas et al., "Combined Optical and Electronic Analysis of Cells with the AMAC Transducers", The (List continued on next page.)

Primary Examiner—Vincent P. McGraw
Assistant Examiner—LaCharles P. Keesee, II
Attorney, Agent, or Firm—Brumbaugh, Graves, Donohue & Raymond

[57] ABSTRACT

An apparatus and method for measuring the volume and hemoglobin concentration of individual red blood cells in a whole blood sample provides for isovolumetrically sphering the red blood cells of the sample using a sphering reagent and forming a stream of individual, spaced-apart cells sheathed in an electrolytic liquid in a flow chamber. The red blood cells in the stream are passed through a light scattering channel in which the intensity of light scattered by each cell into a preselected angular interval in the forward direction is measured. Each cell in the stream is also passed through a resistance pulse sizing aperture for measuring the volume of the cell. The angular interval within which the intensity of scattered light intensity is measured is selected such that for each measured value of scattered light intensity corresponding to a red blood cell and value of the volume of the cell, as determined by the resistance pulse sizing, a unique value of hemoglobin concentration for the cell may be calculated over the entire physiological range of values of cell volume and cell hemoglobin concentration. The values of the cell volume and cell hemoglobin concentration are then used for deriving clinically useful statistical characteristics of the blood sample, such as the mean cell volume, the mean cell hemoglobin concentration, the width of the cell volume distribution and the width of the cell hemoglobin concentration distribution.

18 Claims, 5 Drawing Sheets

OTHER PUBLICATIONS

Journal of Histochemistry and Cytochemistry, 1977, vol. 25, No. 7, pp. 827–835.

V. Kachel, "Electrical Resistance Pulse Sizing (Coulter Sizing)", Flow Cytometry & Sorting, John Wiley 1979, pp. 61–104.

J. A. Steinkamp et al., "Signal Processing Electronics for Multiple Electronic and Optical Measurements on Cells", Cytometry, 1982, vol. 2, No. 4, pp. 232–237.

Y. R. Kim et al., "Isovolumetric Sphering and Erythrocytes for More Accurate and Precise Cell Volume Measurement by Flow Cytometry", Cytometry, 1983, vol. 3, No. 6, pp. 419–427.

J. M. Bator et al., "Erythrocyte Deformability and Size Measured in a Multiparameter System that Includes Impedance Sizing", Cytometry, 1984, vol. 5, pp. 34–41.

W. H. Schuette et al., "Design of Flow Chamber with Electronic Cell Volume Capability and Light Detection Optics for Multilaser Flow Cytometry", Cytometry, 1984, vol. 5, pp. 652–656.

D. H. Tycko et al., "Flow-Cytometric Light Scattering Measurement of Red Blood Cell Volume and Hemoglobin Concentration", Applied Optics, May 1, 1985, vol. 24 No. 9, pp. 1355–1365.

W. H. Reinhart, et al., "Red Cell Rheology in Stomatocyte-Echinocyte Transformation: Roles of Cell Geometry and Cell Shape", Blood, Apr. 1986, vol. 67, No. 4, pp. 1110–1118.

M. M. Wintrobe, et al., "Clinical Hematology", Lea & Febiger, 1981, 8th Edition, pp. 541–610.

D. Pinkel, et al., "Flow Chambers and Sample Handling", Flow Cytometry: Instrumentation and Data Analysis, M. Van Dilla et al. (Eds.), pp. 78–128, Academic Press, London (1985).

R. Barer et al., "Refractometry of Living Cells", Quarterly Journal of Microscopical Science, 95, 399, 1954.

S. Chien, "Principles and Techniques for Assessing Erythrocyte Deformability", Blood Cells, vol. 3, (1977), pp. 71–99.

T. Arnfred et al., "Coulter Counter Model S and Model S-plus Measurements of Mean Erythrocyte Volume (MCV) are Influenced by the Mean Erythrocyte Haemoglobin Concentration (MCHC)", Scand. J. Clin. Lab. Invest. 41, 717 (1981).

N. Mohandas et al., "Inaccuracies Associated With the Automated Measurement of Mean Cell Hemoglobin Concentration in Dehydrated Cells", Blood, vol. 56, No. 1, Jul. 1980, pp. 125–128.

B. Deuticke, "Transformation and Restoration of Biconcave Shape of Human Erythrocytes Induced by Amphiphilic agents and Changes of Ionic Environment", Biochim. Biophys. Acta, 163, (1968), pp. 494–500.

T. Fujii, et al., "Shape Changes of Human Erythrocytes Induced by Various Amphipatic Drugs Acting on the Membrane of the Intact Cells", Biochemical Pharmacology, vol. 28, 1979, pp. 613–620.

C. Bohren, et al., "Absorption and Scattering of Light by Small Particles", John Wiley & Sons, 1983.

APPARATUS AND METHOD FOR MEASURING VOLUME AND HEMOGLOBIN CONCENTRATION OF RED BLOOD CELLS

BACKGROUND

The present invention relates to the measurement of the volume and hemoglobin concentration of individual red blood cells in a whole blood sample and, more particularly, to the making of such measurements for deriving therefrom statistical characteristics of the sample in automated clinical hematology instrumentation.

The red blood cells in a blood sample from a patient are not identical to one another. In each sample, there are statistical distributions of the volumes (V) and of hemoglobin concentrations (HC) of the individual cells. Consequently, the red blood cells in a sample are characterized by the mean cell volume (MCV), the mean cell hemoglobin concentration (MCHC), the width of the V distribution (RDW), and the width of the HC distribution (HDW). These statistical distributions and their associated mean values and widths are used to classify and diagnose anemias. For example, in iron deficiency anemia and in thalassemia MCV is low, MCHC is low, and RDW is high. Hereditary spherocytosis is characterized by an elevated MCHC. In sickle cell anemia the MCHC is normal but HDW is elevated, and the HC distribution is skewed toward high HC values. In hemoglobin SC disease HDW and MCHC are both elevated.

The red cell indices MCV and MCHC of a blood sample can be calculated from a manually measured value of the red cell count (RBC) in the sample, a photometrically measured value of the hemoglobin concentration in the sample as a whole (HGB), and a hematocrit value (HCT) representative of the percent by volume of packed red cells in the sample. These known manual measurement techniques do not provide V or HC distributions, nor the widths of such distributions.

Microscopic examination of a blood smear permits a qualitative evaluation of the distributions of cell size and cell color, the latter being indicative of the hemoglobin concentration of the cells. Various classifications of the observed characteristics of the blood smear are then made. For example, an abnormally wide distribution of sizes is called anisocytosis and abnormally pale cells are labeled hypochromic, as described, for example, in M. Wintrobe et al, "Clinical Hematology", Lea and Febiger, Philadelphia, 1981.

Another known technique for making quantitative measurements of the HC distribution (or cell density profile) is to subject the cells in a sample to centrifugation, during which the cells distribute themselves throughout a column containing a buoyant medium having a density gradient. The resulting cell distribution along the column is then evaluated by photometric techniques.

Automated flow-cytometric hematology instruments are currently used in almost all laboratories and hospitals. Examples of such instruments include the Coulter S+IV by Coulter Electronics, Inc. of Hialeah, Fla.; the H6000 and the H*1 by Technicon Instruments Corporation of Tarrytown, N.Y.; the Celldyne 3000 by Unipath Corporation of Mountain View, Calif.; the ELT-8 by Ortho Instruments Corporation of Westwood, Mass.; the Sysmex M-2000 by Toa Corporation of Japan, and the System 9000 by Sorono-Baker Diagnostics, Inc. of Allentown, Pa. With only one exception, the H*1, these instruments detect and measure only one signal per red blood cell, and this signal is interpreted as being representative of the volume of the cell. Except for the Technicon H*1, no cell-by-cell hemoglobin concentration determination is made by the aforementioned instruments. Thus, such instruments can be used to derive a volume distribution and associated MCV and RDW values, as well as measure RBC and HGB. The value of MCHC must then be calculated from RBC, HGB and MCV using the formula $$MCHC = 1000 \times [HGB/(RBC \times MCV)]. \quad (1)$$

Instruments which do not derive an HC distribution are incapable of determining HDW. The Coulter S+IV, the Celldyne 3000, the Sysmex M-2000 and the System 9000 all utilize the electrical resistance pulse sizing method, commonly referred to as the Coulter principle, for measuring the cell volume. The H6000 and the ELT-8 use a volume determination technique based on measurement of the light scattered by a cell into a single, selected angular interval. The H*1 determines both V and HC using measurements of the light scattered by a sphered red cell into two selected angular intervals.

In instruments based on electrical resistance pulse sizing, individual red cells entrained in an electrolytic fluid medium are made to pass through a relatively small aperture through which an electric current is flowing, as explained, for example, in "Electrical Resistance Pulse Sizing: Coulter Sizing" by V. Kachel in *Flow Cytometry and Sorting*, M. Melamed et al, Eds. Chap. 4, Wiley-Liss, New York, 1990. Because red blood cells are extremely poor conductors of electricity compared with the electrolytic fluid, each time a cell passes through the aperture, a change in electrical resistance of the electrolytic fluid within the aperture is measured by the instrument. The relative change in resistance, $\Delta R/R_o$, is related to the ratio of the volume of the blood cell to the volume of the aperture, $V/V_o$, through the equation $$\Delta R/R_o = f_s(V/V_o), \quad (2)$$

where $R_o$ is the resistance of the electrolytic fluid within the aperture when no red blood cell is being passed, $\Delta R$ is the change in resistance when a cell is being passed through the aperture, $V_o$ is the volume of the aperture and V is the volume of the cell. The quantity $f_s$ depends on the shape of the red blood cell when it is in the aperture and is called the "shape factor".

The higher hydrodynamic forces acting on each cell as it passes through the aperture tend to deform the cell into a prolate spheroid. Theoretical considerations show that the shape factor, $f_s$, varies between 1.0 for a very thin needle-shaped cell and 1.5 for a sphere. The amount of deformation experienced by a given red blood cell depends on its internal viscosity which, in turn, depends primarily on the hemoglobin concentration, HC, within the cell.

The value of HC is known to vary substantially among individual red blood cells in both normal, i.e., HC in the range of 27 to 40 g/dL (g/dL=grams/deciliter), and pathologic, i.e., HC in the range of 25 to 50 g/dL, blood samples. This wide variation in HC results in a correspondingly wide variation in the shape factor, $f_s$, from cell to cell. In each of the above-mentioned instruments which use resistance pulse sizing, the assumption of a constant value for $f_s$ is made, and the empirical cell-to-cell variation in $f_s$ is ignored.

This expedient of assuming a constant $f_s$ follows from the fact that a single measurement of the resistance change $\Delta R$ can only determine the product $f_s \cdot V$, as shown by equation (2). Therefore, by assuming a constant $f_s$ a value for V is easily obtained for each value of $\Delta R$. However, as a result of this assumption, the calculated MCV and the derived MCHC may be inaccurate, especially when the blood sample has a high proportion of cells with extremely low or extremely high hemoglobin concentrations. Cells with lower HCs (i.e., lower internal viscosities) tend to be more needle-like than cells with higher HCs (i.e., higher internal viscosities). Accordingly, the assumption of constant $f_s$ causes the volumes of low HC cells to be underestimated and the volumes of high HC cells to be overestimated Thus, from equation (1) blood samples having many red blood cells with elevated HC values will result in a measured value of MCV which is too high and a derived value of MCHC that is too low. Likewise, if the sample has many red cells with low HC values, the measured value of MCV will be too low and the derived value of MCHC will be too high.

These errors which result from the assumption of a constant $f_s$ in resistance pulse sizing measurements restrict the dynamic range of measured MCHC values relative to the true range of MCHC values. A serious consequence of this so-called MCHC/MCV interference is that present day instruments using resistance pulse sizing do not track variations in MCHC with sufficient accuracy. This introduces a systematic error which reduces the clinical value of MCHC as a red blood cell index, as explained, for example, in N. Mohandas et al, Blood 56, 125, 1980 and T. Arnfred et al: Scand. J. Clin. Lab. Invest. 41, 717, 1981.

In U.S. Pat. No. 4,298,836 to Groves and Coulter, a slit-scanning, time-of-flight optical technique for measuring the length of a cell is combined with resistance pulse detection in an attempt to determine the shape factor $f_s$ for each individual cell as it passes through the sizing aperture. If $f_s$ is known for each cell, an accurate volume could be derived from the resistance pulse signal. However, the length measurement of the cell is made after it leaves the sizing aperture, and owing to the substantial hydrodynamic forces on a cell as it exits a sizing aperture, it is unlikely that the measured cell length is the same as the length of the cell while in the aperture. Furthermore, this patent does not teach any technique for measuring the hemoglobin concentration of individual red blood cells.

An article by Bator et al., Cytometry 5, 34, (1984), describes a technique in which resistance pulse sizing is combined with an ultra high speed photographic technique to record on film images of red blood cells as they exit from the sizing aperture. Cell dimensions and $f_s$ are then determined manually from the photographs to allow corrections to be made to the resistance pulse volume measurements. The technique described in the Bator et al. article is much too slow to be applicable to present-day clinical laboratory instrumentation where typically more than 20,000 red cells per patient sample are counted and sized in 60 seconds or less. Furthermore, the Bator et al. article also does not disclose any technique for measuring the hemoglobin concentration of the individual red blood cells.

The electrical resistance pulse technique has been combined with optical measurements in a number of instances. U.S. Pat. No. 3,710,933 to Fulwyler et al. describes making optical measurements on biological cells after the cells have passed through a resistance pulse sizing aperture. The optical measurements are specified as being measurements of the intensity of forward scattered light within small angular intervals (i.e., angles between 0.5° and 2.0°) and measurements of the intensity of fluorescence emitted by the cells. These measurements do not provide the information required for determining the hemoglobin concentration of red blood cells or for correcting the accuracy of the resistance pulse volume measurements.

In an article by Thomas et al., "Combined Optical and Electronic Analysis of Cells with the AMAC Transducers", J. Histochem. Cytochem 25, 827 (1977), an automated multiparameter analyzer for cells is described in which optical measurements on a particle are carried out while the particle is within the resistance pulse sizing aperture. The only optical measurements described in the article are measurements of the intensity of fluorescence from small beads and leukemic white cells. Such measurements do not provide information for determining the hemoglobin concentration of red blood cells or for correcting resistance pulse volume measurements.

A similar apparatus is described in U.S. Pat. No. 4,198,160 to Kachel et al. The apparatus disclosed in this patent also combines fluorescence measurements with resistance pulse volume measurements. However, the fluorescence measurements, which are used to make determinations of other characteristics of the cells, do not provide the information needed to correct the accuracy of the resistance pulse volume measurements or to determine the hemoglobin concentration of individual red blood cells.

U.S. Pat No. 4,735,504 to the present inventor discloses a technique for determining the volume and hemoglobin concentration of individual red blood cells. The technique described in this patent uses two forward light scattering measurements made using different angular intervals. Because each of two measurements provides scattered light intensity signals which are nonlinear functions of V and HC, this technique has the problem in that extracting the values of V and HC from the two measurements requires extensive computing resources, such as a computer with a high speed arithmetic unit and a large memory. Furthermore, this technique has the disadvantage of the higher complexity and cost associated with having two optical channels.

Accordingly, from the foregoing it is clear that a need exists for an improved apparatus and method for measuring the volume and hemoglobin concentration of individual red blood cells of a blood sample and for deriving useful characteristics of the sample, such as MCV, MCHC, RDW and HDW, without requiring extensive computing resources, and being otherwise less complex and of lower cost.

SUMMARY OF THE INVENTION

The problems and disadvantages of the prior art, as discussed above, are avoided, and the foregoing need is fulfilled by the present invention which in one aspect is an apparatus for measuring the volume and hemoglobin concentration of individual red blood cells in a blood sample which includes provisions for isovolumetrically sphering the red blood cells of the sample. Such sphering of the red blood cells makes it possible to design light scattering measurement systems which have a precisely defined and unambiguous response function, and eliminates or reduces the shape factor, $f_s$, problem in resistance pulse sizing measurements.

The apparatus also includes provisions for entraining the sphered red blood cells of the sample into a stream of spaced-apart, individual, sphered cells sheathed in an electrolytic liquid, and a light source for illuminating each of the red blood cells in the stream with light of predetermined spectral characteristics incident on the cells from a predefined direction. Illumination of each cell by the light source means produces a forward light scattering pattern about the direction of incidence of the illuminating light. The angular intensity distribution of the scattering pattern is dependent upon two fixed system parameters, namely, the wavelength of the incident light and the index of refraction of the electrolytic liquid. In addition, this intensity distribution is dependent upon two red blood cell properties, namely, the index of refraction, which is directly related to the hemoglobin concentration, and the volume of the cell.

Also included in the apparatus are provisions for optical detection and measurement of the intensity of the forward scattered light by each of the red blood cells within a preselected angular interval, and for providing a corresponding first pulse signal having an amplitude, $S_L$, representative of the measured intensity of the light scattered by the cell within the preselected angular interval. Sphering the red blood cells before the light scattering measurement eliminates the shape and orientation dependence of the light scattering, and the volume and hemoglobin concentration of the cell become the sole variable parameters which determine the light scattering pattern. According to the invention, the integrated intensity of the light scattered by the red blood cell is measured within a carefully selected angular interval within the light scattering pattern. This angular interval, once determined, is another fixed system parameter, and is selected such that the measurement of the intensity of the light scattered by a cell within the angular interval, together with the volume of the cell permits the calculation of a unique value of the hemoglobin concentration of the cell.

The apparatus of the invention further includes an aperture of specified cross section and length positioned to pass each of the red blood cells in stream and the sheathing electrolytic liquid, and provisions for measuring the electrical resistance of the electrolytic liquid within the aperture, including a change in the electrical resistance caused by the passing of each of the red blood cells of the stream through the aperture, and for providing a corresponding second pulse signal having an amplitude representative of the change in the electrical resistance caused by the passing of the red blood cells through the aperture. In the preferred embodiment of the invention, two electrodes are positioned on respective sides of the aperture, and a current source connected to the electrodes produces a constant electrolytic current flowing through the electrolytic liquid between the electrodes, including through the aperture.

Because the cross sectional area of the aperture is relatively small compared to that of other regions of the chamber containing the electrolytic liquid on each side of the aperture, the voltage across the electrodes is determined essentially by the resistance of the volume of the electrolytic liquid within the aperture. When a red blood cell passes through the aperture, this electrical resistance abruptly increases to cause a pulsed increase in the voltage across the electrodes. According to the present invention, this pulsed increase in voltage provides a second pulse signal. In general, the amplitude, $S_R$, of the second pulse signal depends on fixed system parameters, such as aperture dimensions, conductivity of the electrolytic liquid and the applied current, as well as on the volume and shape of the red blood cell as it passes through the aperture. Since the red blood cells passing through the aperture have been sphered, the shape factor, $f_s$, in equation (2) has a value of 1.5 for all cells. Consequently, $S_R$ is directly proportional to the volume, V, of the red blood cell passing through the aperture, with a proportionality constant which is a known function of the fixed system parameters.

In addition, the apparatus of the invention includes provisions for determining the volume of each of the red blood cells passing through the aperture from the amplitude, $S_R$, of the corresponding second pulse signal, and further provisions for determining the hemoglobin concentration of each of the red blood cells in the stream from the amplitude, $S_L$, of the corresponding first pulse signal and the volume, V, of the cell determined from the amplitude, $S_R$, of the corresponding second pulse signal. For a sphered red blood cell, the volume of the cell, V, is accurately determined from $S_R$, in the manner described above. Having derived the value of the cell Volume, V, and the amplitude, $S_L$, of the first pulse signal corresponding to the cell, the value of the hemoglobin concentration, HC, may be readily calculated, provided that the angular interval used to obtain $S_L$ is correctly chosen such that for each pair of values of V and $S_L$, a unique value of HC may be calculated. If the cells are illuminated with substantially monochromatic light having a wavelength in the range of 0.5 $\mu$m to 1.0 $\mu$m, the angular interval used to obtain $S_L$ is advantageously defined by a minimum angle, $\theta_L$, and a maximum angle, $\theta_H$, where $\theta_L \geq \theta_l - 2°$, $\theta_H \geq \theta_h$. The angle $\theta_l$ is the angle above which the differential cross section for the scattering of the light by a sphered red blood cell having a volume of 160 fL (fL=femtoliters) is a strictly increasing function of the hemoglobin concentration of the cell, and the angle $\theta_h$ is the angle at which the differential cross section for the scattering of light by a sphered red blood cell is approximately 2% of the maximum differential cross section of such a cell having a hemoglobin concentration of approximately 49 g/dL (g/dL=grams/deciliter) and a volume in the range of 20 to 160 fL. According to the preferred embodiment of the invention, the red blood cells in the stream are illuminated with substantially monochromatic light having a wavelength of 0.6328 $\mu$m and the angular interval used to obtain $S_L$ is defined by $\theta_L \geq 6.5°$ and $\theta_H \geq 25°$.

Having selected a correct angular interval for measuring $S_L$, a table relating HC to V and $S_L$ may be constructed and used to facilitate the computation of the value of HC from the value of V computed using $S_R$, and the value of $S_L$.

The preferred embodiment of the invention also includes provisions for performing statistical analysis such as histogram generation, on the values of cell volume and cell hemoglobin concentration determined in the above-described manner. As mentioned above, statistical distributions (e.g., histograms) of the volumes and hemoglobin concentrations of red blood cells, and their associated mean values and distribution widths are clinically useful, for example in classifying and diagnosing anemias.

In another aspect, the present invention provides a method for measuring the volume and hemoglobin concentration of individual red blood cells in a blood sample which includes the steps described above in connection with the foregoing apparatus.

BRIEF DESCRIPTION OF THE DRAWINGS

The present invetnion may be better understood with reference to the following detailed description of an exemplary embodiment, taken in conjunction with the accompanying drawing, in which.

DETAILED DESCRIPTION

Figure 1:
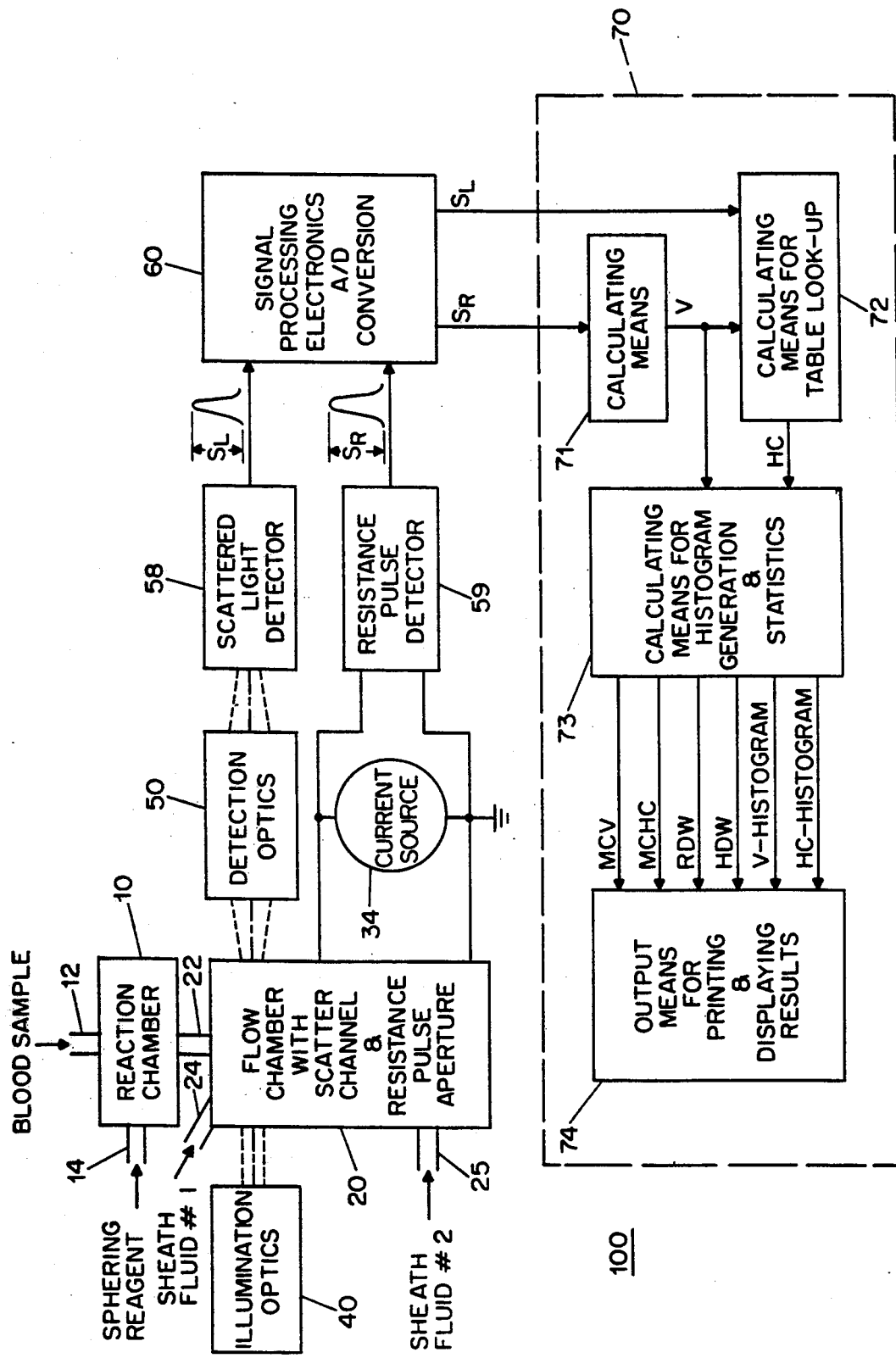
FIG. 1 is a block diagram of an exemplary embodiment of the apparatus according to the invention.

Referring to FIG. 1, there is shown an apparatus 100 for g the volume and hemoglobin concentration of individual red blood cells of a blood sample and for deriving from such measurements statistical characteristics of the blood sample, in accordance with an exemplary embodiment of the invention. A blood sample is introduced into a reaction chamber 10 through a tube 12 from a sampling device (not shown). An isovolumetric sphering reagent is introduced into the reaction chamber 10 through a second tube 14. Many such sphering reagents are known and are described, for example, in T. Fuji et al., "Shape Changes of Human Erythrocytes Induced by Various Amphipathic Drugs", Biochemical Pharmacology 28, 613, (1979), and B. Deuticke, "Transformation and Restoration of Biconcave Shape of Human Erythrocytes by Amphiphilic Agents", Biochim. Biophys. Acta 163, 494, (1968), and U.S. Pat No. 4,412,004 to Ornstein et al.

A sphering reagent transforms red blood cells from their normal biconcave disk shape into spheres by reducing the surface area of the cell membrane to be as small as possible. The excess membrane created during the sphering process is externalized by anionic compounds and internalized by cationic compounds. As reported in W. H. Reinhart and S. Chien, "Red Cell Rheology in Stomatocyte-Echinocyte Transformation: Roles of Cell Geometry and Cell Shape", Blood 67, 1110, (1986), red cells prepared by cationic compounds are more resistant to deformation than those sphered by anionic compounds. Consequently, it is advantageous to use a cationic sphering compound, and chlorpromazine hydrochloride is preferred for the purposes of the present invention. The sphering reagent is an isotonic dilute solution of the sphering compound in phosphate-buffered saline of pH 7.4 and osmolarity of 290 mOsm.

The purpose of isovolumetric sphering in the present invention is twofold. First, since the angular distribution of the light scattered by a cell depends in general on the volume, hemoglobin concentration, shape, and orientation of the cell as it passes through the incident light beam, sphering the red cells eliminates the shape and orientation dependence and allows accurate and precise calculation of the light scattering response as a function of $V$ and HC. As explained below, the present invention requires that such calculations be made. Second, by insuring that all the cells have the same shape (i.e., spheres), the shape factor, $f_s$, of the resistance pulse response function of equation (2) can be given a constant value of 1.5 for all cells without introducing any systematic errors in the determination of $V$.

After the red blood cells and the sphering reagent mix and react in the reaction chamber 10, the diluted sample, now containing isovolumetrically sphered red blood cells, is introduced into a low chamber 20 through a tube 22.

Figure 2:
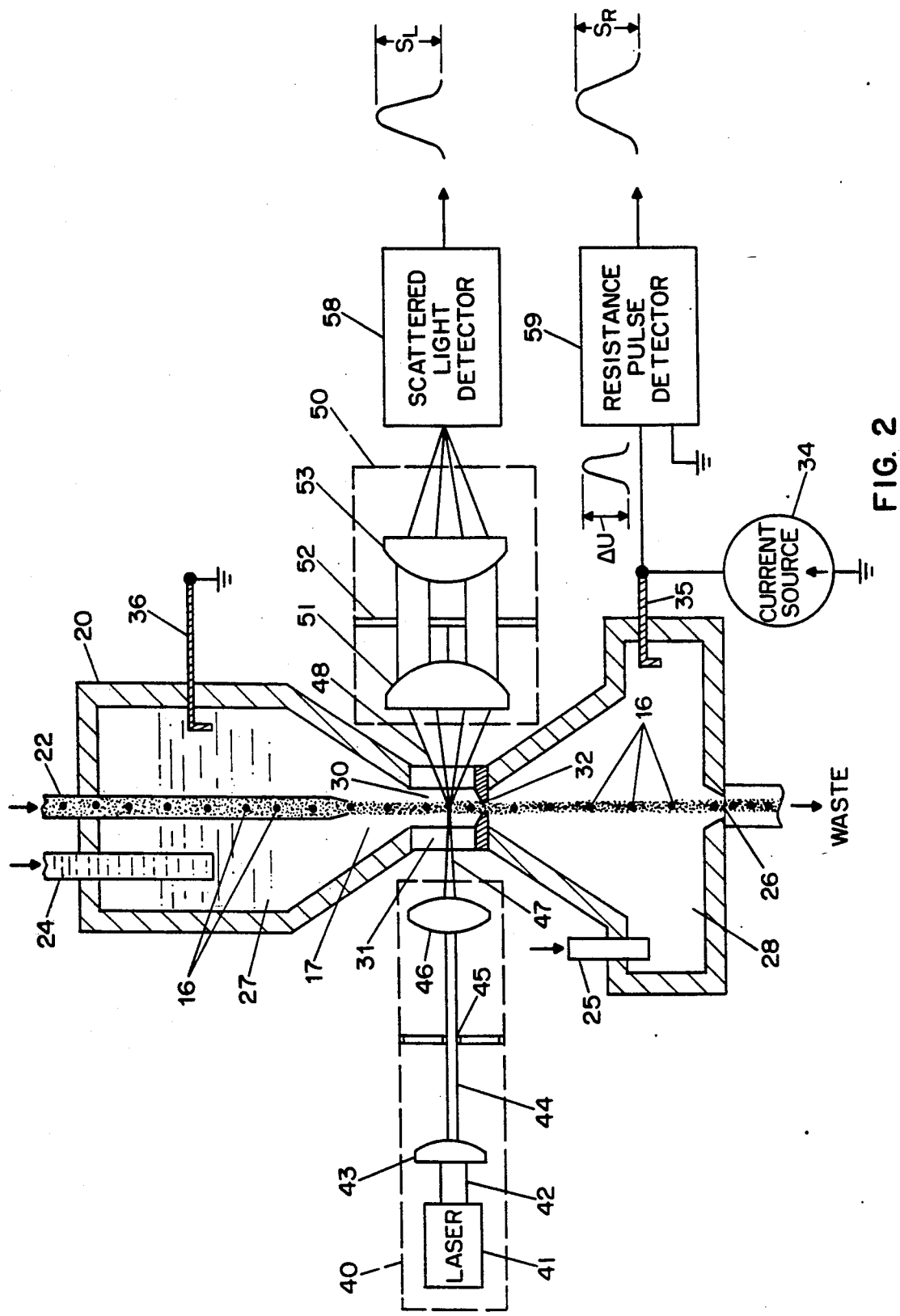
FIG. 2 is a partial cross sectional view and partial block diagram illustrating in greater detail the flow chamber, the illumination optics and the detection optics of the apparatus of FIG. 1.

Turning now to FIG. 2, there is shown a partial sectional view of the flow chamber 20 and details of the illumination optics 40 and the detection optics 50 of the apparatus of FIG. 1. The flow chamber 20 incorporates a number of conventional features relating to hydrodynamic focusing and sheath flow, which are described, for example, in D. Pinkel and R. Stovel, "Flow Chambers and Sample Handling", *Flow Cytometry: Instrumentation and Data Analysis*. M. Van Dilla et al (Eds.), pp. 77–128, Academic Press, London (1985) and the previously cited article by V. Kachel on electrical resistance pulse sizing. It comprises an entrance chamber 27 and an exit chamber 28 connected by two measuring regions, the scatter flow channel 30 and the resistance pulse sizing aperture 32. A particle-free electrolytic liquid, which fills the flow chamber 20, is continuously introduced through conduits 24 and 25, and continuously extracted through an exit orifice 26. The electrolytic liquid is an isotonic phosphate-buffered saline solution of pH 7.4 and osmolarity approximately 290 mOsm. The index of refraction of the electrolytic fluid is made equal to that of the sphering reagent by adjusting the NaCl concentration.

A constant electric current, supplied by a conventional current source 34, flows through the electrolytic fluid in the flow chamber 20 between a platinum electrode 35 in the exit chamber 28 and another platinum electrode 36 in the entrance chamber 27, and passes through the resistance pulse sizing aperture 32. The scatter flow channel 30 is a capillary having a square cross section (typically 200×200 $\mu$m²) with transparent flat walls 31 of optical glass. The resistance pulse sizing aperture 32 is fabricated by drilling a small hole of approximately 70 μm in diameter and 100 μm in length in a sapphire jewel.

The sample entry tube 22, which is made of hypodermic tubing, is aligned on the central axis of the flow chamber 20 so that the sample liquid containing isovolumetrically sphered red blood cells 16 is constrained to a narrow cylindrical axial stream 17 by the flow of the surrounding electrolytic liquid (sheath fluid). The diameter of the cylindrical sample stream 17 varies with the cross sectional area of flow chamber 20 and is controlled by varying the flow rates of the electrolytic sheath fluid and sample liquid (the hydraulic system is not shown). Typically, the sample stream 17 will have a diameter of 25 μm in the scatter flow channel 30 and 10 μm in the resistance sizing aperture 32. Consequently, the spaced-apart, sphered red blood cells 16, which typically have diameters in the 4 μm to 7 μm range, will successively pass through the two measuring regions closely confined to the central axis of the flow chamber 20. This tight control of the lateral position of the cells, commonly called hydrodynamic focusing, is need to achieve the accurate and precise light scattering and resistance pulse measurements required by the present invention.

In the light scattering measurement, the scattering angles subtended by the detection optics 50 are dependent on the lateral position of the red cell from which the light is scattered. As will be explained below, the selection of the angular interval within which the intensity of the scattered light is detected and measured is of crucial importance to the invention.

In the resistance pulse sizing aperture, the electric field is substantially constant in a region near the central axis, and increases rapidly in the radial direction away from the axis. Therefore, accurate resistance pulse sizing measurements also require the cells to be closely confined to the axial region.

As a sphered red blood cell 16 traverses the scatter flow channel 30, it passes through a short section of approximately 10 to 20 μm that is illuminated by a monochromatic light beam of wavelength μ=0.6328 μm produced by a He-Ne laser 41 and the illumination optics 40. A typical configuration for the illumination optics is illustrated in FIG. 2. The circular light beam 42 from the laser 41 is first converted by a cylindrical lens 43 into an elliptical beam 44, which in turn illuminates a rectangular aperture 45. A spherical lens 46 images the rectangular aperture 45 on the axis of the scatter flow channel 30. In this manner, the light beam 47 has a rectangular shape when it intersects the sample stream 17. The rectangular beam shape ensures that all the red blood cells 16 in the scatter flow channel 30 are uniformly illuminated, independent of their radial position within the sample stream 17.

As a sphered red blood cell 16 passes through the light beam 47, a fraction of the incident light is scattered in an angular intensity pattern that is azimuthally symmetric about the propagation direction of the light beam 47. The intensity of the scattered light varies with the angle, $\theta$, between the direction of a ray of scattered light 48 and the direction of the incident light beam 47. The details of the angular variation depend upon the size and optical properties of the cell causing the scattering of the light.

In the theory of light scattering, the angular intensity distribution of the scattered light is represented by the differential scattering cross section, $dC/d\theta$. This function specifies the amount of light (for unit incident irradiance) scattered per unit scattering angle about the conical surface containing all the rays of light scattered in a given direction. A detailed description of such light scattering may be found, for example, in C. F. Bohren & D. R. Huffman, *Absorption and Scattering of Light by Small Particles*, John Wiley & Sons, New York (1983). The isovolumetric sphering of the red blood cells makes it possible to calculate accurately the differential scattering cross section, $dC/d\theta$, using what is commonly called Mie scattering theory by considering the red blood cells as homogeneous dielectric spheres.

A sphered red blood cell can be considered as a homogeneous sphere characterized by a volume V and a complex refractive index $n_c = n_r - in_i$. Variations in $n_c$ from cell to cell can be attributed solely to Variations in HC. The real part of $n_c$ is related to HC by the equation $$n_r = n_0 + (\alpha \cdot HC), \tag{3}$$

where $n_0$ is the refractive index of the cell fluid in the absence of hemoglobin and $\alpha$ is the specific refraction increment of hemoglobin, as explained in greater detail, for example, in R. Barer & S. Joseph "Refractometry of Living Cells", Quarterly Journal of Microscopical Science, 95, 399, 1954. Typically, at wavelengths in the range of 0.6 to 0.9 μm, $n_0$ and $\alpha$ have values of 1.34 and 0.0019 dL/g, respectively. In the same wavelength range, the imaginary part of $n_c$ is given by $$n_i = \frac{\ln 10}{\pi M} \cdot \lambda \cdot \epsilon \cdot HC, \tag{4}$$

where M is the molecular weight of hemoglobin (65,000), $\lambda$ is the wavelength of the illuminating light in μm and $\epsilon$ is the micromolar extinction coefficient of hemoglobin at wavelength $\lambda$ in cm²/micromole. When $\lambda$ is in the range of 0.6 to 0.9 μm, $\epsilon$ is between 0.15 to 0.25 cm²/micromole. Thus, the complex refractive index of a red blood cell is determined using equations (3) and (4) and is dependent on a single physical variable, the cell hemoglobin concentration, HC. It follows from this optical model of a red blood cell that $dC/d\theta$ for a sphered cell is a function of the cell properties V and HC and of known system parameters of the measuring instrument. The latter include the wavelength, $\lambda$, of the illuminating light and the refractive index, $n_s$, of the sample and sheath fluids. The sphering reagent and electrolytic sheath fluids must have the same refractive index. In terms of the Mie scattering theory, $$dC/d\theta = f(\theta, \lambda, n_s, V, HC) = (\pi/k^2)(i_1 + i_2)\sin\theta, \tag{5}$$

where $k = 2\pi n_s/\lambda$, and $i_1$ and $i_2$ are the Mie intensity functions for scattered radiation polarized normal and parallel to the scattering plane, respectively. Computer programs for evaluating the Mie intensity functions $i_1$ and $i_2$ are known and are described, for example, in the book by Bohren and Huffman cited above. Examples of graphical plots of $dC/d\theta$ versus $\theta$ for different cell volumes and wavelengths, and $n_s = 1.334$ are shown in FIGS. 3a, 3b, 3c and 3d. Each of these figures show separate plots for hemoglobin concentrations, HC, of 19, 34 and 49 g/dL, respectively.

The light scattered into an angular interval between two angles $\theta_L$ and $\theta_H$ (measured with respect to the direction of incidence of the illuminating light) is collected by the detection optics 50 and converted to an electrical pulse by the scattered light detector 58 yielding for each cell 16 in the stream 17, a scatter pulse signal of amplitude $S_L$. The amplitude $S_L$ is the height of the electrical pulse from light detector 58 and is a measure of the radiant power of the light scattered by the sphered red blood cell into the angular interval between $\theta_L$ and $\theta_H$.

In accordance with the invention, the angular interval defined by $\theta_L$ and $\theta_H$ must be chosen such that the light scattering measurement of $S_L$ and the resistance pulse measurement of the volume, V, corresponding to a red blood cell, in combination, determine a unique value of hemoglobin concentration, HC, for the cell over the entire physiological ranges of V and HC. It is not sufficient to choose such an angular interval that only applies to narrow ranges of V and HC. It should be appreciated that there exists a range (or possibly more than one range) of such angular intervals which satisfy the above-described criterion.

Figure 3A:
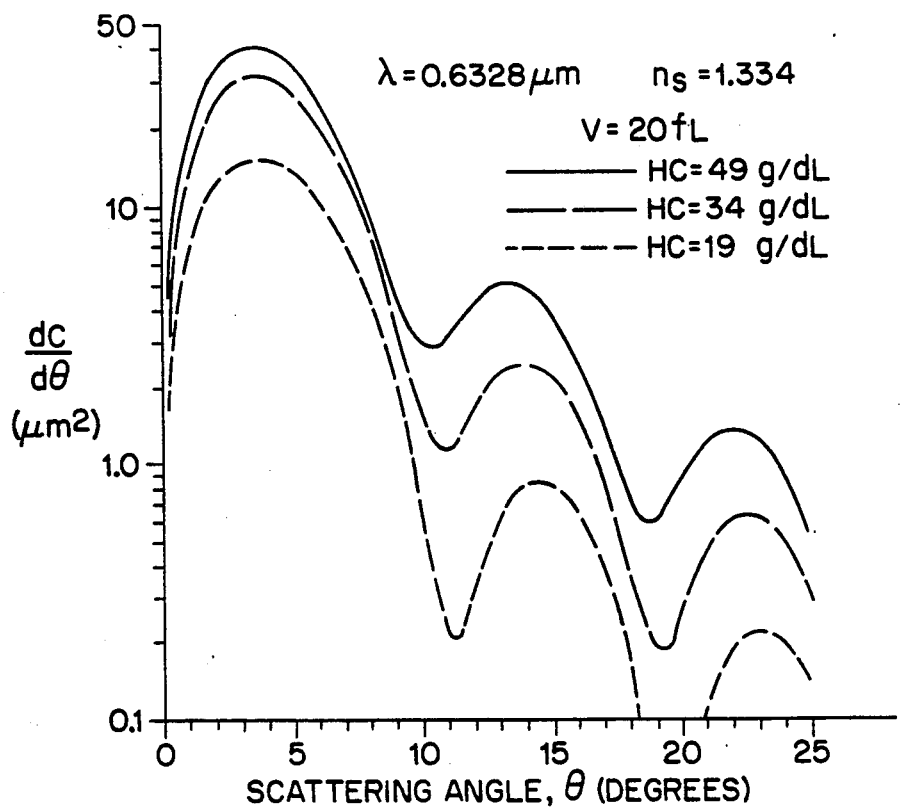
FIGS. 3A, 3B, 3C and 3D are each graphical plots of the differential light scattering cross section, $dC/d\theta$, for sphered red blood cells versus the scattering angle, $\theta$, for hemoglobin concentrations, HC, of 19, 34 and 49 g/dL, the four figures representing $\mu = 0.6328$ $\mu$m and $V = 20$ fL, $\lambda = 0.6328$ $\mu$m and $V = 90$ fL, $\lambda = 0.6328$ $\mu$m and $V = 160$ fL, and $\lambda = 0.840$ $\mu$m and $V = 160$ fL, respectively.
Figure 3B:
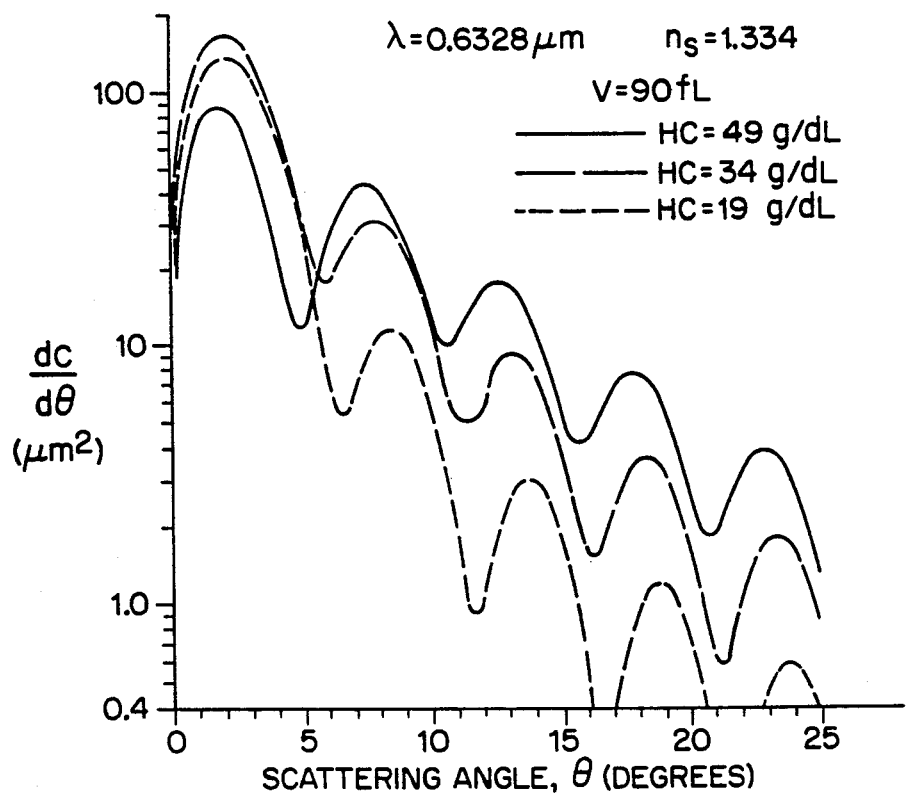
Figure 3C:
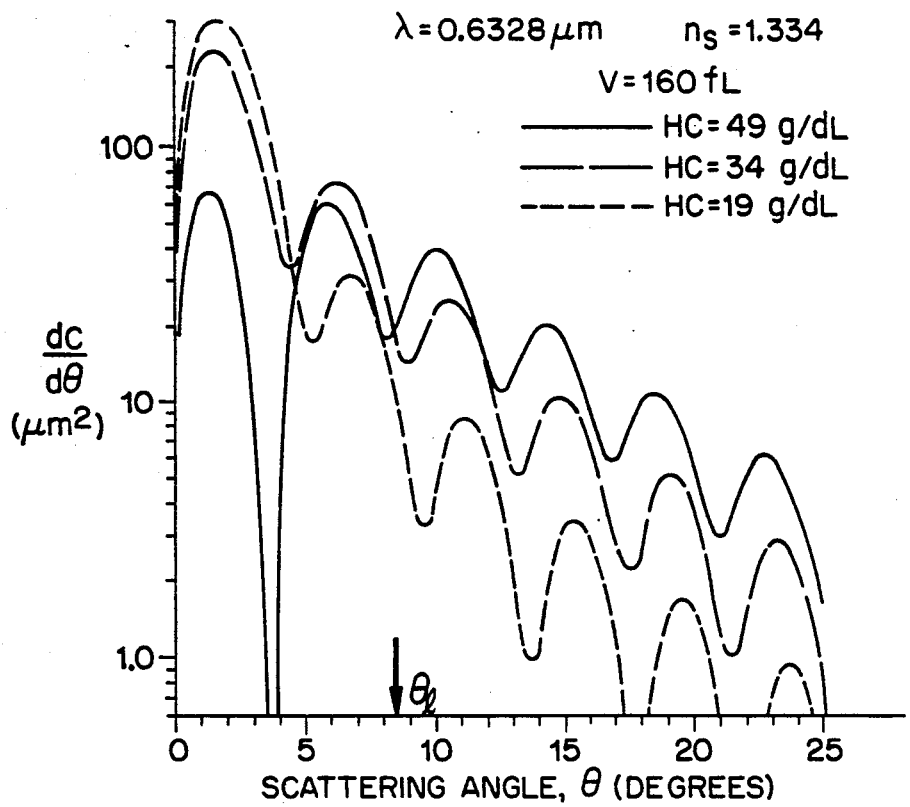
Figure 3D:
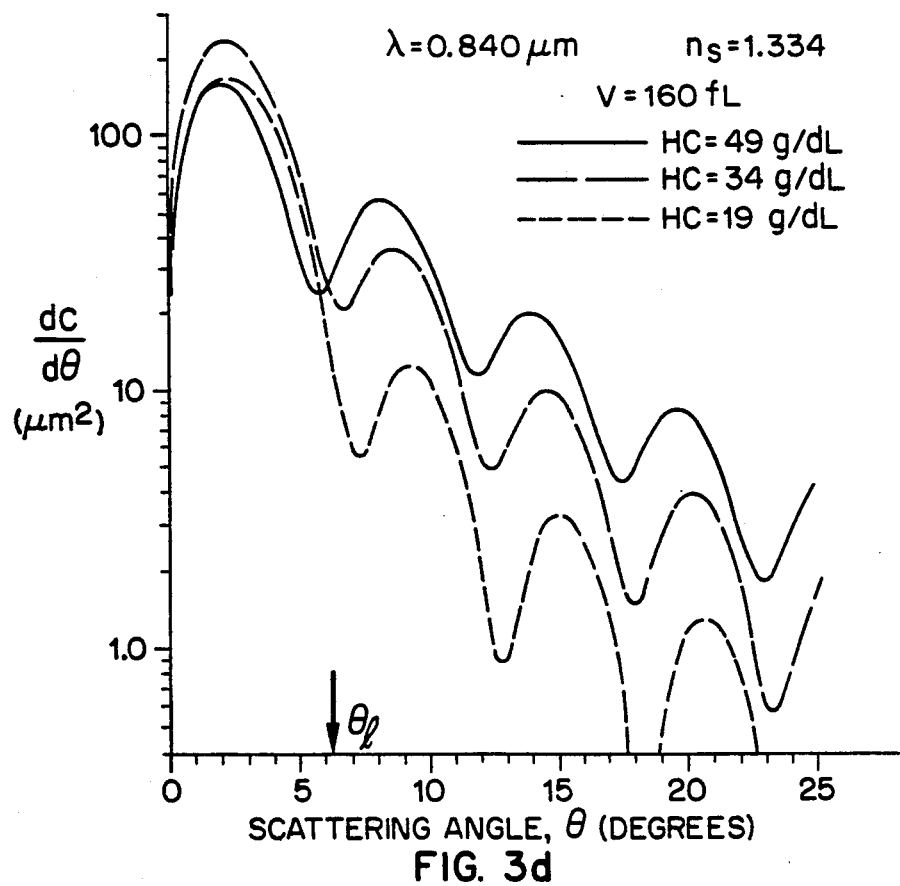

The requirement that $S_L$ and V corresponding to a cell, in combination, determine a unique value of HC for the cell can be expressed precisely in terms of the mathematical properties of $S_L$. The functional dependence of the scatter signal amplitude $S_L$ on V, HC, and on instrumental system parameters $\theta$, $n_s$, $\theta_L$ and $\theta_H$ can be calculated by integrating the differential scattering cross section $dC/d\theta$ over the angular interval between $\theta_L$ and $\theta_H$, i.e., $$S_L(V, HC, \lambda, n_s, \theta_L, \theta_H) = K \int_{\theta_L}^{\theta_H} \left(\frac{dC}{d\theta}\right) d\theta, \quad (6)$$

where K is a constant proportionality factor which takes into account the intensity of the illuminating light and the response function of the detection optics 50 and the scattered light detector 58. Such integrals can be evaluated numerically with high precision using well known computational techniques. Considering $S_L$ as a function of V and HC, the requirement that $S_L$ and V unambiguously determine HC will be satisfied if for any fixed value of V in the physiological range of V, $S_L$ is a strictly increasing (or strictly decreasing) function of HC over the physiological range of HC. It follows from equation (6) that $S_L$ will certainly have this property if for any V in the physiological range of V and any $\theta$ between $\theta_L$ and $\theta_H$, $dC/d\theta$ is a strictly increasing (or strictly decreasing) function of HC over the physiological range of HC. In FIGS. 3a-3c, $dC/d\theta$ is plotted against $\theta$ for $\lambda=0.6328$ μm and values of V and HC spanning their respective physiological ranges. These curves show that at this wavelength, $dC/d\theta$ increases with increasing HC for all values of $\theta$ between 8.5° and 25° and for all values of V between 20 fL and 160 fL, the physiological range of V. Therefore, at this wavelength any angular interval that satisfies the condition $$8.5° \geq \theta_L < \theta_H \geq 25° \quad (7)$$

yields a light scatter signal amplitude $S_L$ with the required functional dependency on V and HC to provide a unique value of HC for each pair of values of $S_L$ and V. In particular, the angular interval defined by $\theta_L=8.5°$ and $\theta_H=25°$ will meet this requirement.

Figure 4:
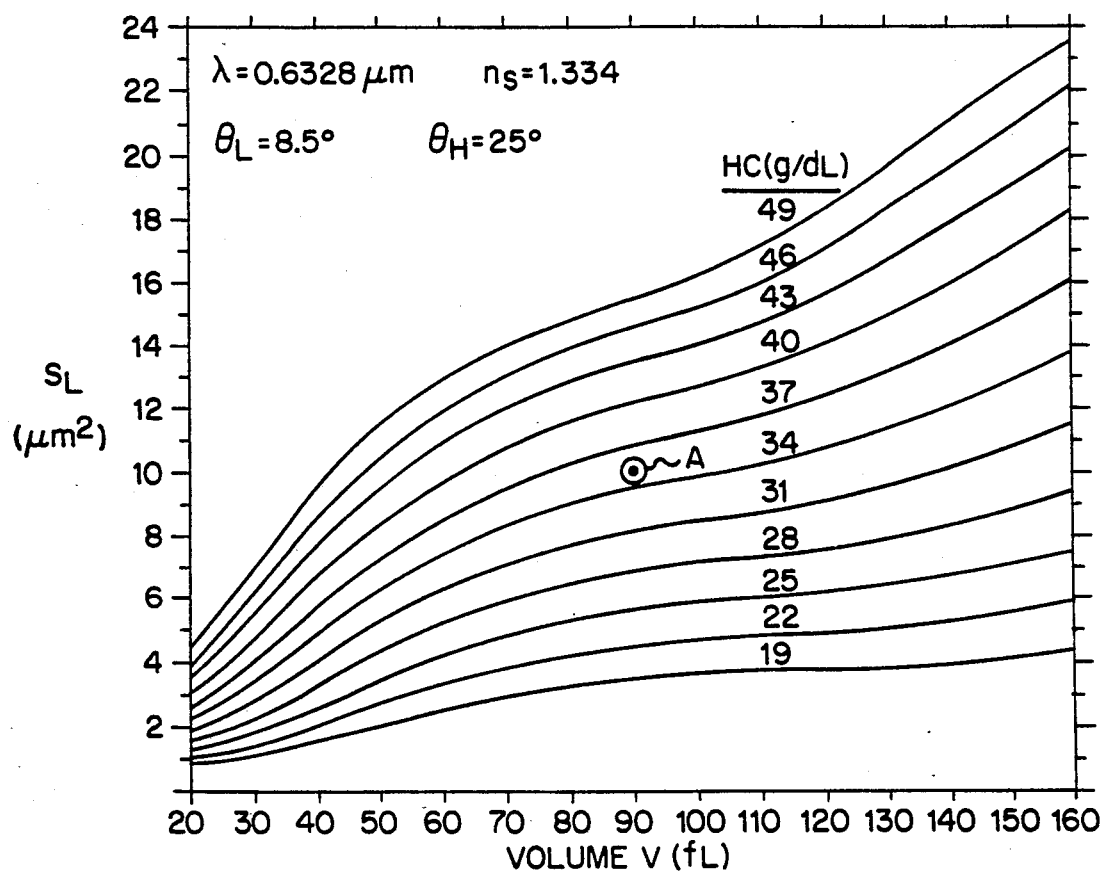
FIG. 4 are graphical plots of the amplitude of the scattered light signal, $S_L$, versus the cell volume, $V$, for hemoglobin concentrations, HC, of 19, 22, 25, 28, 31, 34, 37, 40, 43, 46 and 49 g/dL, respectively, the scattered light signal amplitude, $S_L$, having been calculated for an angular interval between $\theta_L = 8.5°$ and $\theta_H = 25°$ and an illumination wavelength of $\lambda = 0.6328$ $\mu$m, the graphical plots showing that for the angular interval used in the calculation, there exists a unique value of HC corresponding to each pair of values of $V$ and $S_L$.

In FIG. 4 there is shown a graphical plot of the value of $S_L$, calculated using equation (6) for the angular interval defined by $\theta_L=8.5°$ and $\theta_H=25°$, plotted against V for various values of HC within its physiological range. As expected, $S_L$ increases with increasing HC for all values of V. The unique correspondence between HC values and respective pairs of $S_L$ and V values is evident in FIG. 4 from the clear separation of the curves representing the different values of HC. A unique, unambiguous value of the HC can therefore be calculated from each pair of measured values of V and $S_L$, where the value of $S_L$ is measured using an angular interval selected in accordance with the invention. For example, suppose the light scattering measurement and the resistance pulse volume measurement on a sphered red blood cell yielded $S_L=10$ μm² and V=90 fL, respectively. These values of V and $S_L$ are indicated by the circled point A in FIG. 4 located between the HC=34 g/dL and HC=37 g/dL curves. Interpolation yields the value of HC=34.8 g/dL. This unambiguous one-to-one correspondence between respective pairs of V and $S_L$ values and HC values allows the construction of a table of HC values against $S_L$ and V values that can be stored in the memory of a data analyzing computer to facilitate the calculation of HC.

In general, for wavelengths between 0.5 μm and 1.0 μm, $\theta_L$ and $\theta_H$ are chosen according to the relations $$\theta_L \geq \theta_l, \text{ and } \theta_H \geq \theta_h, \quad (8)$$

where $\theta_l$ is the angle above which $dC/d\theta$ for V = 160 fL is a strictly increasing function of HC, and $\theta_h$ is the angle above which there are negligible contributions to the scattering signal $S_L$. Advantageously, $\theta_h$ is selected as the angle at which $dC/d\theta$ is approximately 2% of its maximum value when the sphered red blood cell has a hemoglobin concentration of 49 g/dL and a volume in the range of 20 to 160 fL.

In general, $\theta_L$ may be chosen as much as 2° lower than $\theta_l$ provided that $\theta_H$ is not less than $\theta_h$. For example, when $\lambda=0.6328$ μm, $\theta_L$ can be lowered from 8.5° to 6.5° and $S_L$ will still have the required functional behavior (i.e., well separated curves for different values of HC provided that $\theta_H \geq 25°$). As another example, when $\lambda=0.840$ μm and $\theta_l=6.25°$, selecting $\theta_L=6.25°$ and $\theta_H=25°$ yields $S_L$ curves with the required separations for different values of HC. In this case, $\theta_L$ can be lowered to 4.25° and the separation is maintained provided $\theta_H$ is not reduced.

Figure 5:
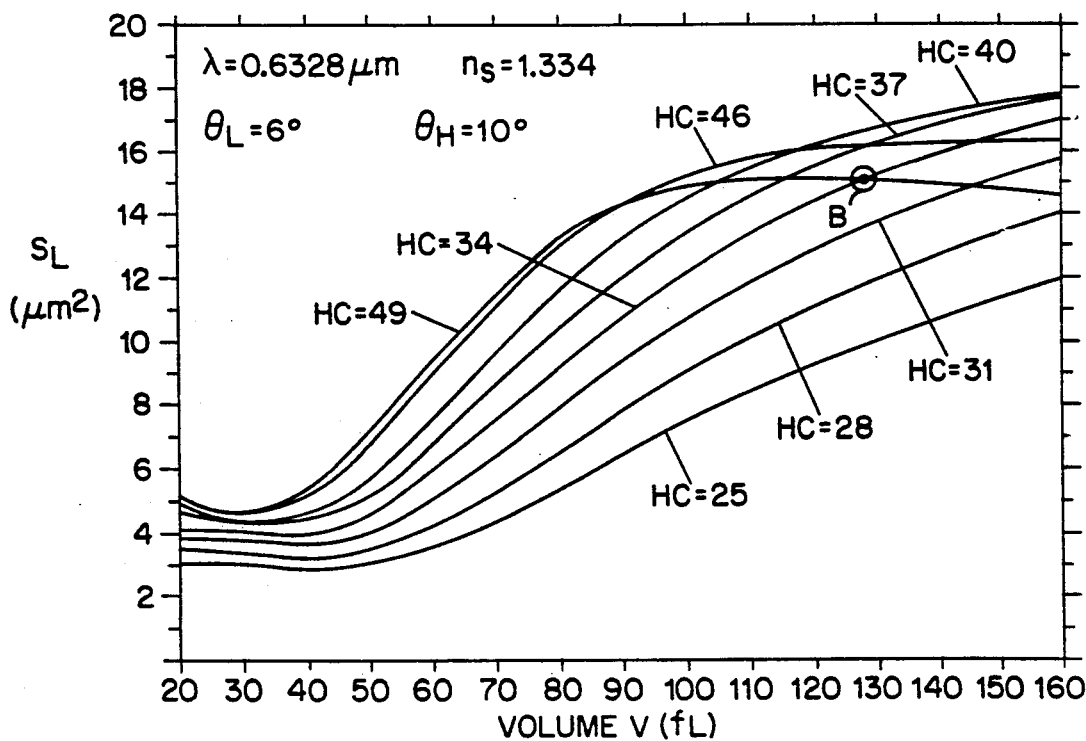
FIG. 5 are graphical plots of the amplitude of the scattered light signal, $S_L$, versus the cell volume, $V$, for the same hemoglobin concentrations as in the graphical plots of FIG. 4, the scattered light signal amplitude, $S_L$, having been calculated for an angular interval between $\theta_L = 6°$ and $\theta_H = 10°$ and an illumination wavelength of $\lambda = 0.6328$ $\mu$m, the graphical plots of this figure showing that for the angular interval used in the calculation, there does not always exist a unique value of HC corresponding to each pair of values of $V$ and $S_L$.

If $\theta_L$ and $\theta_H$ are not selected according to the invention in the manner described above, the resulting $S_L$ values will not provide the required unambiguous one-to-one correspondence between HC values and pairs of V and $S_L$ values. For example, if $\lambda=0.6238$ μm and one chooses $\theta_L=6°$ and $\theta_H=10°$, an angular interval which does not satisfy the requirements of equation (8), the $S_L$ curves obtained using such an angular interval are shown in FIG. 5. The bunching and crossing of the curves associated with different values of HC results in the loss of the one-to-one correspondence between values of HC and respective pairs of values of V and $S_L$. For example, the circled point B in FIG. 5 has coordinates of V=128 fL, $S_L=15$ μm², but corresponds to both HC=34 g/dL and HC=49 g/dL by virtue of being at the intersection of the curves for those HC values. Therefore, if these were the measured values for V and $S_L$, a unique value for HC could not be determined because the angular interval used for measuring $S_L$ was not selected in accordance with the invention.

Referring again to FIG. 2, the detection optics 50 comprises a spherical collection lens 51, an annular dark-stop 52 for defining the angular interval for measuring $S_L$, and a focusing lens 53. The light scattered by a sphered red blood cell 16 is collected and collimated by lens 51. The unscattered portion of the illuminating light beam 47 also passes through lens 51. The collimated light from lens 51 impinges upon the annular dark-stop 52. The latter is a thin flat optical element that is completely opaque except for a clear circular annulus centered on the optical axis. The inner and outer radii of the clear annulus are chosen to correspond to the scattering angles $\theta_L$ and $\theta_H$, respectively. Thus, light scattered at angles outside the interval between $\theta_L$ and $\theta_H$ will be absorbed by the annular dark-stop 52, as will the unscattered portion of the incident light beam 47.

Only light scattered into the angular interval between $\theta_L$ and $\theta_H$ passes through the annular dark-stop 52. Lens 53 focuses the light transmitted by the annular dark-stop 52 onto the scattered light detector 58.

The scattered light detector 58 comprises a photosensitive device, such as a silicon photodiode or a photomultiplier tube, followed by a linear amplifier of conventional design. The scattered light detector 58 converts each pulse of scattered light from detection optics 50 into an electrical signal pulse having height $S_L$.

After passing through the light beam 47, each of the sphered red blood cells 16 is transported through the electrical resistance pulse sizing aperture 32. A constant current, I, supplied by a current source 34 of conventional design, flows through the electrolytic sheathing liquid in the flow chamber 20 from the electrode 35 (anode) to the electrode 36 (cathode) and passes through the aperture 32. The electrical resistance of the electrolytic sheathing liquid along the current path results in a voltage drop between the electrodes 35 and 36. Since the cross sectional area of the aperture 32 is much smaller than that of the other regions of the flow chamber 20 along the current path, the electrical resistance between electrodes 35 and 36 is essentially the electrical resistance, $R_0$, of the volume of electrolytic liquid within the aperture 32.

The passage of a sphered red blood cell 16 through the aperture 32 produces a pulsed increase $\Delta R$ in the electrical resistance between electrodes 35 and 36. This pulsed increase in electrical resistance results in a concomitant pulsed increase $\Delta U$ in the voltage sensed at electrode 35. Using equation 2, the pulsed increased in the voltage $\Delta U$ may be expressed as $$\Delta U = I\Delta R\left(\frac{IR_o}{V_o}\right)f_s V, \quad (9)$$

where $R_o$ and $V_o$ are the electrical resistance and volume of the aperture, respectively, and V is the volume of the cell that caused $\Delta U$ by passing through the aperture 32.

The resistance pulse detector 59, which is essentially a linear amplifier of conventional design with a very high input impedance, amplifies the pulsed voltage increase $\Delta U$ at electrode 35 to provide a voltage signal pulse having a height $S_R$. From equation (9), $S_R$ may be expressed as $$S_R = G\Delta U = cf_s V, \quad (10)$$

where G is the voltage gain of the resistance pulse detector 59 and c is a proportionality factor which depends only on system parameters I, $R_o$, $V_o$, and G of the measuring instrument.

As discussed above, the shape factor $f_s$ has the value 1.5 for all the sphered red blood cells and is independent of cell volume. The hydrodynamic forces experienced by a sphered red blood cell 16 as it traverses the resistance pulse sizing aperture 32 do not deform the cell appreciably because the spherical shape cannot be changed without increasing the cell membrane surface area, a process which requires forces that are approximately 10,000 times greater than those needed to deform untreated red cells with biconcave disk shapes. Further details of the deformability of red blood cells may be found, for example, in S. Chien, "Principles and Techniques for Assessing Erythrocyte Deformability", Blood Cells 3, 71, (1977). Therefore, $f_s$ may be considered a constant having a value of 1.5, and the resistance pulse sizing signal amplitude, $S_R$, may be treated as being strictly proportional to the volume V of the sphered red blood cell that produced the signal.

Although the measurements of the hemoglobin concentration, HC, and the volume, V, of a red blood cell in accordance with the invention will be most accurate if the cells maintain their spherical shapes while traversing the resistance pulse sizing aperture 32, there may be instances where hydrodynamic forces will cause slight deformations of the spherical cell shape since the deformability of a sphered cell depends to some extent on the chemical reagent used to transform the cell shape to that of a sphere. Such small deformations will generally introduce only a small uncertainty in the shape factor, $f_s$, and cause only small errors in the measurement of cell volume. However, an advantageous feature of the present invention is that the accuracy of the measurement of hemoglobin concentration is not affected as much by such deformations as the measurement of cell volume. The relative error in HC due to a relative error in V can be estimated from the $S_L$ versus V plots of FIG. 4. From FIG. 4, it is apparent that for volumes in the range of 55 to 125 fL and hemoglobin concentrations in the range of 28 to 40 g/dL, $$\Delta HC/HC < 0.5(\Delta V/V). \quad (11)$$

That is, measurements of HC will be at least twice as accurate as measurements of V over the most important ranges of V and HC values.

Referring again to FIG. 1, the two signal pulses having amplitudes $S_L$ and $S_R$ are directed to the signal processing electronics 60, which performs the following tasks. First, the validity of the pulses are confirmed by comparing their heights and widths to predetermined thresholds and limits, respectively. Second, since the light scattering signal pulse precedes the resistance signal pulse in time, the signal processing electronics also confirms that the time interval separating the two pulse signals is within a predetermined acceptable range. Third, the peak heights $S_L$ and $S_R$ of the two signal pulses are detected, held, and converted to corresponding digital numbers $\hat{S}_L$ and $\hat{S}_R$. The signal processing electronics 60 comprises electronic gates, delays, sample-and-hold circuits, analog-to-digital converters, and digital buffer registers of conventional design.

The two pulse signal amplitudes $S_L$ and $S_R$, now in digital form, are transmitted to a data analyzing computer 70. Calculating means 71 receives the digital form of the resistance pulse signal amplitude $S_R$ and calculates the value of the volume V of the associated sphered red blood cell using the formula $$V = CS_r \qquad (12)$$

where C is a previously determined calibration constant that is stored in the memory of the computer 70. The calibration constant C can be determined by passing spherical particles of a known volume through the system. Such particles having volumes in the red cell volume range are commercially available. Equation (12) follows from equation (10) because of the constancy of $f_s$ for sphered red cells.

Calculating means 72 receives the digital form of light scattering signal pulse height $S_L$ and the value of V provided by calculating means 71. As discussed above, precomputed look-up tables relating HC values to respective pairs of V and $S_L$ values are stored in the computer memory. Calculating means 72 searches this HC versus V and $S_L$ table, and performs any necessary interpolation to derive the HC value corresponding to the values of V and $S_L$ it received.

The value of HC and the corresponding value of V are transmitted to calculating means 73, which uses such values to generate the V and HC histograms for the current blood sample. When the last red blood cell of the sample has been measured, calculating means 73 calculates the means and standard deviations of the two histograms to derive the MCV, MCHC, RDW, and HDW values for the blood sample. These results and the V and HC histogram data are transmitted to output means 74 for printing on report forms and for displaying on a video display unit.

While the invention has been described in terms of the foregoing specific embodiment thereof, it will be apparent to those skilled in the art that various alterations and modifications may be made to the described embodiment without departing from the scope of the invention, as defined by the appended claims. For example, with appropriate modifications to the flow chamber 20 or the resistance pulse sizing aperture 32, the resistance pulse measurement may take place upstream from the light scattering measurement, or the two measurements may be made substantially concurrently.

I claim:

1. An apparatus for measuring the volume and hemoglobin concentration of individual red blood cells in a blood sample comprising:

means for isovolumetrically sphering the red blood cells of the sample;

means for entraining the sphered red blood cells of the sample into a stream of spaced-apart, individual, sphered red blood cells sheathed in an electrolytic liquid;

light source means for illuminating each of the red blood cells in the stream with light of predetermined spectral characteristics incident from a predefined direction;

optical detection means for measuring within a preselected angular interval the intensity of light scattered in the predefined direction by each of the red blood cells illuminated by the light source means and providing a corresponding first pulse signal having an amplitude representative of the measured intensity of the light scattered by the red blood cell, the preselected angular interval being chosen to permit the calculation of a unique value for the hemoglobin concentration of each red blood cell in the stream from the measured intensity of the light scattered by the cell and the volume of the cell;

an aperture of specified cross section and length positioned to pass each of the red blood cells in the stream and the electrolytic liquid by which the stream is sheathed;

resistance measuring means for measuring the electrical resistance of the electrolytic liquid within the aperture, including a change in the electrical resistance caused by the passing of each of the red blood cells in the stream through the aperture, and providing a corresponding second pulse signal having an amplitude representative of the change in the electrical resistance caused by the passing of the cell through the aperture;

first calculating means for determining the volume of each of the red blood cells in the stream passing through the aperture from the corresponding second pulse signal; and second calculating means for determining the hemoglobin concentration of each of the red blood cells of the stream from the corresponding first pulse signal and the volume of the cell determined by the first calculating means from the corresponding second pulse signal.

2. An apparatus according to claim 1, wherein the light source means is for illuminating the red blood cells of the stream with substantially monochromatic light having a predetermined wavelength $\lambda$ and the preselected angular interval, within which the intensity of the light scattered by each of the illuminated red blood cells is measured, is defined by a minimum angle, $\theta_L$, and a maximum angle, $\theta_H$, the first pulse signal provided by the optical detection means having an amplitude $S_L$ which is related to volume, V, and hemoglobin concentration, HC, of the corresponding red blood cell by an equation $$S_L = K \int_{\theta_L}^{\theta_H} \left( \frac{dC}{d\theta} \right) d\theta,$$

where K is a constant proportionality factor and $dC/d\theta$ is the differential cross section for the scattering of light of wavelength $\lambda$ in the predefined direction by a spherical red blood cell having a volume V and a hemoglobin concentration HC, and wherein $\theta_L$ and $\theta_H$ are selected such that when $S_L$ is calculated using the equation, a unique value of HC is obtained for each combination of values of V and $S_L$, at least for values of V in the range of 20 to 160 fL.

3. An apparatus according to claim 2, wherein $\theta_L$ and $\theta_H$ are selected such that when $S_L$ is calculated using the equation and graphs of $S_L$ versus V are plotted for respective values of HC, a graph of $S_L$ versus V for one value of HC does not intersect a graph of $S_L$ versus V for another value of HC, at least for values of V in the range of 20 to 160 fL.

4. An apparatus according to claim 1, wherein the light source means is for illuminating the red blood cells of the stream with substantially monochromatic light having a predetermined wavelength in the range of 0.5 $\mu$m to 1.0 $\mu$m and the preselected angular interval within which the light scattered by each of the illuminated red blood cells is measured is defined by a minimum angle, $\theta_L$, and a maximum angle, $\theta_H$, where $\theta_L \geq \theta_l - 2°$, $\theta_H \geq \theta_h$, $\theta_l$ being the angle above which the differential cross section for the scattering of the light by an illuminated spherical red blood cell having a volume of 160 fL is a strictly increasing function of the hemoglobin concentration of the cell, and $\theta_h$ being the angle at which the differential cross section for the scattering of the light by an illuminated spherical red blood cell is approximately two percent of the maximum light scattering differential cross section of such a red blood cell having a hemoglobin concentration of approximately 49 g/dL and a volume in the range of 20 to 160 fL.

5. An apparatus according to claim 1, wherein the light source means is for illuminating the red blood cells of the stream with substantially monochromatic light having a wavelength of 0.328 μm, and the detection means is for measuring the intensity of scattered light within an angular interval defined by a minimum angle, $\theta_L$, greater than or equal to 8.5° and a maximum angle, $\theta_H$, less than or equal to 25°.

6. An apparatus according to claim 1, wherein the illumination of each of the red blood cells of the stream by the light source means occurs before the passing of the red blood cell through the aperture.

7. An apparatus according to claim 1, wherein the illumination of the red blood cells of the stream by the light source means takes place in spatial proximity to the position of the aperture.

8. An apparatus according to claim 1, wherein the means for isovolumetrically sphering the red blood cells of the sample comprises a reaction chamber receiving the sample and a sphering reagent, and the means for entraining the sphered red blood cells of the sample comprises a sheathed stream flow chamber receiving the sphered red blood cells from the reaction chamber and the electrolytic liquid, the flow chamber having walls with respective transparent regions for passing the light from the light source means for illuminating the red blood cells of the stream and for passing the light scattered by the red blood cells of the stream towards the optical detection means, and wherein the flow chamber is separated into first and second volume regions by the aperture, the first and second volume regions having relatively large cross sections compared to the cross section of the aperture, and the resistance measuring means includes first and second electrodes respectively disposed in the first and second volume regions.

9. An apparatus of claim 1, further comprising third calculating means responsive to the volumes and hemoglobin concentrations determined by the first and second calculating means for performing statistical analysis on such values.

10. A method for measuring the volume and hemoglobin concentration of individual red blood cells in a blood sample comprising the steps of:
  isovolumetrically sphering the red blood cells of the sample;
  entraining the sphered red blood cells of the sample into a stream of spaced-apart, individual, sphered red blood cells sheathed in an electrolytic liquid;
  illuminating the red blood cells in the stream with light of predetermined spectral characteristics incident from a predefined direction;
  measuring within a preselected angular interval the intensity of light scattered in the predefined direction by each of the illuminated red blood cells in the stream and deriving a corresponding first pulse signal having an amplitude representative of the measured intensity of the light scattered by the red blood cell, the preselected angular interval being chosen to permit the calculation of a unique value for the hemoglobin concentration of each red blood cell in the stream from the measured intensity of the light scattered by the cell and the volume of the cell;
  passing the stream of sphered red blood cells and the electrolytic liquid by which the stream is sheathed through an aperture of specified cross section and length positioned in the path of the stream;
  measuring the electrical resistance of the electrolytic liquid within the aperture, including measuring a change in the electrical resistance caused by the passing of each of the red blood cells of the stream through the aperture, and deriving a corresponding second pulse signal having an amplitude representative of the change in the electrical resistance caused by the passing of the red blood cell through the aperture;
  calculating the volume of each of the red blood cells of the stream passing through the aperture from the corresponding second pulse signal; and
  calculating the hemoglobin concentration of each of the red blood cells of the stream from the corresponding first pulse signal and the volume of the cell calculated from the corresponding second pulse signal.

11. Method according to claim 10, wherein the step of illuminating the red blood cells of the stream includes illuminating the cells with substantially monochromatic light having a predetermined wavelength $\lambda$, and the step of measuring the intensity of light scattered in the predefined direction by each of the illuminated red blood cells includes measuring the intensity of scattered light within a preselected angular interval defined by a minimum angle, $\theta_L$, and a maximum angle, $\theta_H$, and the first pulse signal having an amplitude $S_L$ which is related to the volume, V, and hemoglobin concentration, HC, of the corresponding red blood cell by an equation $$S_L = K \int_{\theta_L}^{\theta_H} (dC/d\theta)\, d\theta,$$

where K is a constant proportionality factor and $dC/d\theta$ is the differential cross section for the scattering of light of wavelength $\lambda$ in the predefined direction by a spherical red blood cell having a volume V and a hemoglobin concentration HC, and wherein $\theta_L$ and $\theta_H$ are selected such that when $S_L$ is calculated using the equation, a unique value of HC is obtained for each combination of values of V and $S_L$, at least for values of V in the range of 20 to 160 fL.

12. A method according to claim 11, wherein $\theta_L$ and $\theta_H$ are selected such that when $S_L$ is calculated using the equation and graphs of $S_L$ versus V are plotted for respective values of HC, a graph of $S_L$ versus V for one value of HC does not intersect a graph of $S_L$ versus V for another value of HC, at least for values of V in the range of 20 to 160 fL.

13. A method according to claim 10, wherein the step of illuminating the red blood cells of the stream includes illuminating the cells with substantially monochromatic light having a predetermined wavelength in the range of 0.5 μm to 1.0 μm, and the step of measuring the intensity of light scattered in the predefined direction by each of the illuminated red blood cells includes measuring the intensity of scattered light within a preselected angular interval defined by a minimum angle, $\theta_L$, and a maximum angle, $\theta_H$, where $\theta_L \geq \theta_l - 2°$, $\theta_H \geq \theta_h$, $\theta_l$ being the angle above which the differential cross section $dC/d\theta$ for the scattering of the light by an illuminated spherical red blood cell having a volume of 160 fL is a strictly increasing function of the hemoglobin concentration of the cell, and $\theta_h$ being the angle at which the differential cross section $dC/d\theta$ for the scattering of the light by an illuminated spherical red blood cell is approximately 2% of the maximum light scattering differential cross section of such a red blood cell having a hemoglobin concentration of approximately 49 g/dL and a volume in the range of 20 to 160 fL.

14. A method according to claim 10, wherein the step of illuminating the red blood cells of the stream includes illuminating the cells with substantially monochromatic light having a wavelength of 0.6328 μm, and the step of measuring the intensity of the light scattered by each of the illuminated red blood cells includes measuring the scattered light within an angular interval defined by a minimum angle, $\theta_L$, greater than or equal to 8.5° at a maximum angle, $\theta_H$, less than or equal to 25°.

15. A method according to claim 10, wherein the step of illuminating each of the red blood cells of the stream occurs before the step of passing the red blood cell through the aperture.

16. A method according to claim 10, wherein the step of illuminating each of the red blood cells of the stream takes place in spatial proximity to the position of the aperture.

17. A method according to claim 10, wherein the step of isovolumetrically sphering the red blood cells of the sample includes combining the sample with a sphering agent in a reaction chamber, the step of entraining the sphered red blood cells of the sample into a stream sheathed in an electrolytic liquid includes introducing the sphered red blood cells of the sample into a flow of the electrolytic liquid in a sheathed stream flow chamber, the step of illuminating each of the red blood cells in the stream includes directing a relatively narrow beam of light at the stream of red blood cells through a transparent region of the flow chamber, the step of measuring the intensity of light scattered by each of the illuminated red blood cells of the stream includes detecting the scattered light through another transparent region of the flow chamber, and the step of measuring the electrical resistance of the electrolytic liquid within the aperture includes measuring the electrical resistance between first and second electrodes respectively disposed in first and second volume regions of the flow chamber separated by the aperture.

18. A method according to claim 10, further comprising the step of performing statistical analysis on the calculated volumes and hemoglobin concentrations of the red blood cells in the stream.

* * * * *

UNITED STATES PATENT AND TRADEMARK OFFICE
CERTIFICATE OF CORRECTION

PATENT NO. : 5,194,909            Page 1 of 2

DATED : March 16, 1993

INVENTOR(S) : Daniel H. Tycko

It is certified that error appears in the above-identified patent and that said Letters Patent is hereby corrected as shown below:

Col. 6, line 27, "Volume" should read -- volume --. Col. 7, line 8, "invetnion" should read -- invention --; line 22, "$\mu$" should read -- $\lambda$ --; line 49, "for g" should read -- for measuring --. Col. 8, line 34, "low chamber" should read -- flow chamber --. Col. 9, line 41, "$\mu$" should read -- $\lambda$ --. Col. 10, line 15, "Variations" should read -- variations --. Col. 11, line 24, "$\theta$" should read -- $\lambda$ --; line 58, "$8.5° \geq \theta_L < \theta_H \geq 25°$" should read -- $8.5° \leq \theta_L < \theta_H \leq 25°$ --; line 68, "Within" should read -- within --. Col. 12, line 32, "Which" should read -- which --; line 43, "With" should read -- with --.

UNITED STATES PATENT AND TRADEMARK OFFICE
CERTIFICATE OF CORRECTION

PATENT NO. : 5,194,909
DATED : March 16, 1993
INVENTOR(S) : Daniel H. Tycko

It is certified that error appears in the above-identified patent and that said Letters Patent is hereby corrected as shown below:

Col. 13, line 50, $$\text{"} \Delta U = I \, \Delta R \left(\frac{IR_o}{V_o}\right) f_s V \text{ ,"} \text{ should read}$$

$$-- \Delta U = I \, \Delta R = \left(\frac{IR_o}{V_o}\right) f_s V , \; --.$$

Col. 14, line 3, "Value" should read -- value --. Col. 15, line 3, "V = $CS_r$," should read -- V = $CS_R$, --. Col. 17, line 16, "0.328" should read -- 0.6328 --.

Signed and Sealed this

Eleventh Day of January, 1994

Attest:

BRUCE LEHMAN

*Attesting Officer*    *Commissioner of Patents and Trademarks*